United States Patent
Faergemann et al.

(10) Patent No.: US 10,413,555 B2
(45) Date of Patent: Sep. 17, 2019

(54) TREATMENT OF SKIN ATROPHY WITH A COMBINATION OF TRIIODOTHYROACETIC ACID (TRIAC) AND DEHYDROEPIANDROSTERONE (DHEA)

(71) Applicant: TROPHEA DEVELOPMENT AB, Helsingborg (SE)

(72) Inventors: Jan Faergemann, Göteburg (SE); Gudmundur Johannsson, Halmstad (SE); Claes Ohlsson, Västra Frölunda (SE); Derek Gregory Batcheller, Brussels (BE); Jörgen Johnsson, Helsingborg (SE); Jan Törnell, Västra Frölunda (SE)

(73) Assignee: TROPHEA DEVELOPMENT AB, Helsingborg (SE)

( * ) Notice: Subject to any disclaimer, the term of this patent is extended or adjusted under 35 U.S.C. 154(b) by 0 days.

(21) Appl. No.: 15/528,882

(22) PCT Filed: Nov. 24, 2015

(86) PCT No.: PCT/EP2015/077401
§ 371 (c)(1),
(2) Date: May 23, 2017

(87) PCT Pub. No.: WO2016/083325
PCT Pub. Date: Jun. 2, 2016

(65) Prior Publication Data
US 2017/0319598 A1   Nov. 9, 2017

(30) Foreign Application Priority Data
Nov. 25, 2014   (DK) .................................. 2014 70737

(51) Int. Cl.
*A61K 31/5685* (2006.01)
*A61K 8/06* (2006.01)
(Continued)

(52) U.S. Cl.
CPC ............ *A61K 31/5685* (2013.01); *A61K 8/06* (2013.01); *A61K 8/062* (2013.01); *A61K 8/365* (2013.01); *A61K 8/63* (2013.01); *A61K 9/0014* (2013.01); *A61K 9/06* (2013.01); *A61K 9/107* (2013.01); *A61K 31/192* (2013.01); *A61K 45/06* (2013.01); *A61P 17/00* (2018.01); *A61P 17/02* (2018.01); *A61P 17/06* (2018.01); *A61P 17/08* (2018.01); *A61P 17/10* (2018.01); *A61P 17/16* (2018.01); *A61P 17/18* (2018.01); *A61Q 19/00* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 2004/0009196 A1 | 1/2004 | Ferraris et al. | |
| 2005/0271739 A1 | 12/2005 | Wang | |
| 2010/0009970 A1 | 1/2010 | Johansen et al. | |

FOREIGN PATENT DOCUMENTS

| | | |
|---|---|---|
| CH | 642851 A5 | 5/1984 |
| CN | 1706479 A | 12/2005 |

(Continued)

OTHER PUBLICATIONS

International Search Report dated Jan. 7, 2016 in application No. PCT/EP2015/077401.
(Continued)

*Primary Examiner* — Layla Soroush
(74) *Attorney, Agent, or Firm* — Foley & Lardner LLP

(57) ABSTRACT

The aim of the present study was to investigate the effect of a combination of triiodothyroacetic acid (TRIAC) and dehydroepiandrosterone (DHEA) compared with TRIAC, DHEA or placebo alone on corticosteroid induced effect on collagen synthesis in humans. Six healthy male human volunteers aged 40-65 participated. Four areas of abdominal skin were pre-treated for 3 weeks with betamethasone valerate cream. The same areas were then treated with one of the following alternatives in the same cream vehicle: TRIAC, DHEA, TRIAC+DHEA and placebo for 2 weeks. Then suction blisters were raised in each of these areas with a vacuum pump. The blister fluid from each area was collected and frozen until analysis. Analysis of amino terminal propeptide of human type I procollagen (PINP) in suction blister fluid was performed using a commercially available immunoassay (Orion Diagnostics) kit. This study has for the first time shown that a combination of TRIAC and DHEA could effectively stimulate collagen synthesis in skin pretreated with betamethasone valerate demonstrated by an increase in PINP, and that the combination was more effective than TRIAC or DHEA alone. This combination could be used to effectively treat skin atrophy in corticosteroid induced skin atrophy. It could also be used to treat skin atrophy due to other circumstances such as e. g. sun damaged skin and skin atrophy due to high age. Another interesting application would be to combine TRIAC and DHEA with a potent corticosteroid in order to prevent corticosteroid induced skin atrophy. If this combination still is effective in the treatment of eczema and psoriasis and without the risk of skin atrophy this combination will be a major breakthrough for the use of potent topical corticosteroids.

10 Claims, No Drawings

(51) Int. Cl.

| | | |
|---|---|---|
| A61Q 19/08 | (2006.01) | |
| A61Q 19/00 | (2006.01) | |
| A61P 17/18 | (2006.01) | |
| A61K 8/365 | (2006.01) | |
| A61K 8/63 | (2006.01) | |
| A61K 9/00 | (2006.01) | |
| A61K 9/06 | (2006.01) | |
| A61K 9/107 | (2006.01) | |
| A61K 31/192 | (2006.01) | |
| A61K 45/06 | (2006.01) | |
| A61P 17/00 | (2006.01) | |
| A61P 17/02 | (2006.01) | |
| A61P 17/06 | (2006.01) | |
| A61P 17/08 | (2006.01) | |
| A61P 17/10 | (2006.01) | |
| A61P 17/16 | (2006.01) | |

(56) References Cited

FOREIGN PATENT DOCUMENTS

| EP | 0 831 769 B1 | 10/2003 |
|---|---|---|
| EP | 0 831 769 B2 | 7/2008 |
| WO | WO-94/01398 A1 | 1/1994 |
| WO | WO-99/15210 A2 | 4/1999 |
| WO | WO 2008/154294 A1 | 12/2008 |

OTHER PUBLICATIONS

International Preliminary Report on Patentability issued in related International Patent Application No. PCT/EP2015/077401, dated Jun. 8, 2017.
Bentin et al., "TriAC (3,5,3'-Triiodothyroacetic acid) induced pseudohypothyroidism", Acta Clin. Belg. (1984) vol. 39 (5) pp. 285-289.
Bracco et al., "Comparison of the Metabolic and Endocrine Effects of 3,5,3'-Triiodothyroacetic Acid and Thyroxine", J. Clin. Endocrinol. Metab. (1993), vol. 77, No. 1, pp. 221-228.
Burger et al., "The effects of tetraiodothryoacteic and triiodothyroacetic acids on thyroid function in euthyroid and hyperthyroid subjects", Acta Endocrinologica (Nov. 1979) vol. 92 (3) pp. 455-467.
Calvo et al., "Pangenomic changes induced by DHEA in the skin of postmenopausal women", J. Steriod Biochem. Mol. Biol. (Dec. 2008) vol. 112(4-5) pp. 186-193.
Chopra "Nature, Source, and Relative Significance of Circulating Thyroid Hormones", Werner and Ingbar's the Thyroid, Seventh Edition, (Lippincott-Raven Philadelphia) Chapter 7 (1996) pp. 111-124.
"Triacana", Directonaire Vidal (1975) 51st Edition (O.V.P., Paris) pp. 1753.
El-Alfy M., "Skin responses to topical dehydroepiandrosterone: implications in antiageing treatment?" Br J Dermatol. (Nov. 2010); vol. 163(5), pp. 968-976.
Faergemann et al., "Dose-response Effects of Tri-iodothyroacetic Acid (TriAc) and Other Thyroid Hormone Analogs on Glucocorticoid Induced Skin Atrophy in the Haired Mouse", Acta Derm Venereol (2002) vol. 82 pp. 179-183.
Gniadecki et al. "The effects of KH-1060, a potent 20 epi analogue of the vitamin D3 hormone, on hairless mouse skin in vivo", Br. J. Dermatol. (Jun. 1995) vol. 132(6) pp. 841-852.
Gniadecki et al., "Inhibition of glucocorticoid-induced epidermal and dermal atrophy with KH-1060—a potent 20 epi-analogue of 1,25-dihydroxyvitamin D3.", Br. J. Pharmacol. (1994) vol. 113 pp. 439-444.
Leonard et al., "Intracellular Pathways of Iodothyronine Metabolism", Werner and Ingbar'S the Thyroid, Seventh Edition, (1996) Chapter 8 (Lippincott-Raven, Philadelphia) pp. 125-161.
Nouveau et al., "Effects of topical DHEA on aging skin: a pilot study", Maturitas (2008) vol. 59 pp. 174-181.
Product information on Tricana ills (1962) and Triacana cream (1975).
Rall et al.,"Metabolic Effects in Man of the Acetic Acid Analogues of Thyroxine and Triiodothyropnine", J. Clin. Endocrinol. Metab. (1956) vol. 16 pp. 1299-1310.
Safer et al., "Topical Triiodothyronine Stimulates Epidermal Propiferation, Dermal Thickening and Hair Growth in Mice and Rats", Thyroid (2001) vol. 11 (8), pp. 717-724.
Schwartz et al. "In vivo prevention of corticosteroid-induced skin atrophy by tretinoin in the hairless mouse is accompanied by modulation of collagen, glucosaminoglycans, and fibronection", J. Invest. Dermatol. (Feb. 1994)vol. 102(2), pp. 241-246.
Vahlquist et al., "Inefficacy of topical thyroid hormone analogue TriAc in plaque psoriasis: results of a double-blind placebo-controlled trial", Br. J. Dermatol. (Aug. 2004) vol. 151 (2), pp. 489-491.
Yazdanparast et al., A Thyroid Hormone Analogue, Triiodothyroacetic Acid, Corrects Corticosteroid-Downregulated Collagen Synthesis:, Thyroid (2004) vol. 14 pp. 345-353.
Yazdanparast et al., "Action of Topical Thyroid Hormone Analogue, Triiodothyroacetic Acid in Reversing Glucocorticoid-Induced Skin Atrophy in Humans", Thyroid (2006) vol. 16(11), pp. 1157-1162.
Yazdanparast et al., "Action on Topical Thyroid Hormone Analogues on Glucocorticoid-Induced Skin Atrophy in Mice", Thyroid (2006) vol. 16 (3), pp. 273-280.
Examination Report dated Apr. 5, 2019 in corresponding Russian Application No. 2017121884.
Examination Report dated Mar. 21, 2019 in corresponding Chinese Application No. 201580063734.7.
Mills et al., "The Sex Steroid Precursor DHEA Accelerates Cutaneous Wound Healing Via the Estrogen Receptors," J. Invest. Dermatol. vol. 125, pp. 1053-1062 (2005).
Zhang et al., "Thyroid Hormone Analogue Stimulates Keratinocyte Proliferation but Inhibits Cell Differentiation in Epidermis," International Journal of Immunopathology and Pharmacology, vol. 25, No. 4, pp. 859-869 (2012).

TREATMENT OF SKIN ATROPHY WITH A COMBINATION OF TRIIODOTHYROACETIC ACID (TRIAC) AND DEHYDROEPIANDROSTERONE (DHEA)

FIELD OF THE INVENTION

The present invention relates to the use of a combination of triiodothyroacetic acid (TRIAC) and dehydroepiandrosterone (DHEA) in the treatment of skin atrophy. The combination of TRIAC and DHEA provides an unexpected, synergistic effect.

BACKGROUND OF THE INVENTION

It is well-known that topical treatment with corticosteroids causes skin atrophy as a side effect. However, effective treatment of skin atrophy caused by potent corticosteroids is currently not available.

Skin atrophy involves a reduction in epidermal and dermal thickness, regression of sebaceous glands, loss of subcutaneous fat and muscle-layer atrophy. Typically, such changes can be seen 2 to 3 weeks after initiating treatment with moderate- to highpotency topical corticosteroid use. The affected areas are normally skin with high permeability such as face, but may occur anywhere the application of the corticosteroid takes place. Atrophy may also be seen after application of low-potency corticosteroids and is often reversed upon termination of the treatment. However, in many cases the atrophy is a permanent manifestation that is not reversed Attempts to develop alternative treatments to corticosteroids with another pharmacological approach have been done, but as of today only a few alternative with lower antiinflammatory activity than corticosteroids are available. These treatment modalities consist of vitamin A and D derivatives and calcineurin inhibitors e. g. tacrolimus.

The present invention provides a combination of TRIAC and DHEA, which can be used to effectively treat skin atrophy, for example skin atrophy induced by the use of corticosteroids or prolonged exposure to sunlight.

DETAILED DESCRIPTION OF THE INVENTION

The present invention relates to the use of a combination of TRIAC and DHEA in the treatment of skin atrophy, notably skin atrophy induced by the use of corticosteroids or prolonged exposure to sunlight. The invention also relates to compositions comprising TRIAC and DHEA. The compositions are designed for topical administration to the skin. A combination of TRIAC and DHEA is shown to have synergistic effect in the treatment of skin atrophy.

TRIAC and DHEA, in combination, may also be used or be provided in compositions together with one or more corticosteroids.

Combination of TRIAC and DHEA

As demonstrated in the examples herein the present inventors have for the first time shown that a combination of TRIAC and DHEA could effectively stimulate intact N-terminal propeptide of type I procollagen (PINP) synthesis in skin pretreated with betamethasone valerate and that the combination was more effective than TRIAC or DHEA alone. This combination could be used to effectively treat skin atrophy in corticosteroid induced skin atrophy. It could also be used to treat skin atrophy due to other circumstances such as e. g. sun damaged skin and skin atrophy due to ageing. Another interesting application would be to combine TRIAC and DHEA with a potent corticosteroid in order to prevent corticosteroid-induced skin atrophy. It is envisaged that such a combination may be effective in the treatment of eczema and psoriasis and without the risk of skin atrophy this combination will be a major breakthrough for the use of potent topical corticosteroids.

As an effective treatment of skin atrophy caused by corticosteroids is not available today. However, it would be advantageous to develop such a product. The present invention provides a novel approach in this regard. The effect in patients with clinically verified atrophy can primarily be evaluated using sonography to evaluate skin thickness during treatment with TRIAC and DHEA cream/gel. Efficacy could also be evaluated by biopsies, clinical rating scale and patient rating scale. Adverse events should be recorded. Thyroid hormone levels in plasma are used to monitor systemic effects of TRIAC and measurement of DHEA-sulfate can be used to monitor possible systemic effects of DHEA.

As mentioned above the present invention relates to the use of a combination of TRIAC and DHEA as well as to composition for topical use containing TRIAC and DHEA. As demonstrated in the examples, the combination of TRIAC and DHEA exhibits a higher efficacy in the treatment of skin atrophy than any of the pharmacologically active components (i.e. TRIAC and DHEA) used alone. Said efficacy is preferably measured as PINP production in suction blister fluid from skin. More details appear from the examples herein.

The present invention provides a combination of triiodothyroacetic acid (TRIAC) and dehydroepiandrosterone (DHEA) for use in improving the skin of a subject. In the present context the term "improving the skin of a subject" is intended to mean that the skin to be improved is; skin subject to skin atrophy, sun damaged skin, intrinsically aged skin, eczema and psoriasis, actinic skin damage, intrinsically aged skin, photodamaged skin, lichen planus, ichthyosis, acne, psoriasis, wrinkled skin, Darier's disease, eczema, atopic dermatitis, seborrheic dermatitis sclerooderma, collagen deficient skin, corticosteroid atrophy induced by systemic, inhaled and topical glucocorticoid administration, chloracne, pityriasis, and skin scarring.

Notably, the combination of TRIAC and DHEA is for the treatment or prevention of skin atrophy.

The most common cause of skin atrophy is sun induced atrophy and—as mentioned in the background of the invention—due to treatment with a corticosteroid. In general, corticosteroids are used in skin diseases like dermatitis, atopic dermatitis, rash, and eczema. Skin atrophy may also occur after systemic administration or inhalation of corticosteroids.

Weaker topical steroids are utilized for thin-skinned and sensitive areas, especially areas under occlusion, such as on the face, eyelids, diaper area, perianal skin, and intertrigo of the groin or body folds. Moderate steroids are used for atopic dermatitis, nummular eczema, xerotic eczema, lichen sclerosis et atrophicus of the vulva, scabies (after scabiecide) and severe dermatitis. Strong steroids are used for psoriasis, lichen planus, discoid lupus, chapped feet, lichen simplex chronicus, severe poison ivy exposure, alopecia areata, nummular eczema, and severe atopic dermatitis in adults.

To prevent tachyphylaxis, a topical steroid is often prescribed to be used on a week on, week off routine. Some recommend using the topical steroid for 3 consecutive days on, followed by 4 consecutive days off. Long-term use of topical steroids can lead to secondary infection with fungus or bacteria (see tinea incognito), skin atrophy, telangiectasia (prominent blood vessels), skin bruising and fragility (Burton J L, Lovell C R. Cutaneous atrophy. CH 44: "Disorder of Connective Tissue". In Rook, Wilkinson, Ebling: Textbook of Dermatology. Edited by Champion R H, Burton J L, Burns D A, Breathnach S M. Vol 3, 6 edition. Blackwell Science Ltd., Oxford, 1998, pp. 2004-2018).

Topical corticosteroids are classified after potency, class I being the mildest and class IV the strongest. The classification may vary from country to country.

Group I
 The weakest class of topical steroids.
 Hydrocortisone marketed as 2.5% cream, lotion, and ointment)
 Hydrocortisone marketed as 1%
Group II
 Clobetasone
 Hydrocortisone 17-butyrate
 Triamcinolone acetonide
Group III
 Fluocinonide 0.05%
 Halcinonide 0.05%
 Amcinonide 0.05%
 Desoximetasone 0.25%
 Betamethasone valerate*
 Betametasone dipropionate
 Mometasone furoate
Group IV
 Very potent: up to 600 times stronger than hydrocortisone
 Clobetasol propionate 0.05%
 Halobetasol propionate 0.05%
 Diflorasone diacetate 0.05%
*50-100 times as potent as hydrocortisone Any corticosteroid—such as those mentioned above—may be combined with TRIAC and DHEA in order to prevent or treat a skin conditions as mentioned herein. Moreover, TRIAC and DHEA may be added to any of the existing products such as those mentioned above.

Dosage

The dosage and dosing frequency of a combination of the invention will depend on the particular topical composition, and the identity and severity of the skin disorder to be treated.

Normally, a composition of the invention will contain from about 0.005 to about 2% w/w of TRIAC, notably from about 0.01 to about 0.5% w/w of TRIAC.

Normally, a composition of the invention contains from about 0.5 to about 5% of DHEA, notably from about 1 to about 3% w/w of DHEA.

| DHEA (% w/w) | TRIAC (% w/w) | Ratio DHEA/TRIAC |
| --- | --- | --- |
| 0.5 | 0.005 | 100 |
| 0.5 | 2 | 0.25 |
| 5 | 0.005 | 1000 |
| 5 | 2 | 2.5 |
| 1 | 0.005 | 200 |
| 1 | 2 | 0.5 |
| 3 | 0.005 | 600 |
| 3 | 2 | 1.5 |
| 0.5 | 0.01 | 50 |
| 0.5 | 0.5 | 1 |
| 5 | 0.01 | 500 |
| 5 | 0.5 | 10 |
| 1 | 0.01 | 100 |
| 1 | 0.5 | 2 |
| 3 | 0.01 | 300 |
| 3 | 0.5 | 6 |

As seen from the table above, the weight ratio between DHEA and TRIAC in a combination or composition according to the invention is from about 0.25 to about 1,000 such as from about 0.5 to about 600. Moreover, the ratio may be from about 1 to about 500 or from about 1.5 to about 300. The weight ratio may also be from about 2 to about 200 or from about 2.5 to about 100. A range of suitable weight ratio between DHEA and TRIC can be constructed from any of the numbers mentioned in the above table, i.e. any combination is within the scope of the present application.

A particular interesting ratio is from about 10 to about 200 such as from about 30 to about 150 or from about 50 to about 100. As seen from the examples herein a composition containing DHEA and TRIAC in a weight ratio of 2/0.03=66.7 has been used and demonstrated to have synergistic effect. Thus an even more narrow weight range of interest is from about 60 to about 75 or from about 60 to 70.

Normally, TRIAC is applied in an amount of from about 0.1 to about 50 microgram/cm$^2$ skin surface and DHEA is applied in an amount of from about 10 to about 1000 microgram/cm$^2$ skin surface. As mentioned above the amounts of DHEA and TRIAC are adjusted so that the weight ratio between DHEA and TRIC is within the ranges mentioned above or calculated from the above-mentioned numbers.

In the examples herein TRIAC is applied in an amount of 1.5 microgram/cm$^2$ skin surface and DHEA in an amount of 100 microgram/cm$^2$ skin surface corresponding to a weight ratio between DHEA and TRIAC of from about 66 to about 67.

Compositions

The combination of the invention is delivered to the affected area of the skin in a composition containing the combination of TRIAC and DHEA in a topically acceptable vehicle. As used herein, a topically acceptable vehicle is a vehicle that is acceptable to apply to the skin surface for topical or dermal delivery of the combination of TRIAC and DHEA.

The combination of the invention may be included in any composition suitable for application to the skin. Thus, a composition of the invention is not limited to a specific dosage form or a specific formulation type. The specific dosage form or specific type of formulation chosen does not negatively influence the efficacy of the combination when applied to the skin. Examples of dosage forms and formulations suitable for application to the skin and examples of how to prepare such compositions can be found in Remington's Pharmaceutical Sciences eg 18$^{th}$ edition, Mack Publishing Company, 1990 and later editions to which reference is made.

The present invention provides a topical composition in the form of an ointment, a cream, a lotion, a liniment or other spreadable liquid or semi liquid preparation, a solution, a dispersion, an emulsion such as micro-emulsion, oil-in-water emulsion or waterin-oil emulsion, a suspension, a gel, liposomes, a sprayable composition, an aerosol, a film, powders, washes, shampoos etc.

As mentioned above, the composition may be in the form of an emulsion. Creams and lotions are normally examples of compositions that are in the form of an emulsion. An emulsion is a dispersed system comprising at least two immiscible liquid phases (an oil phase and an aqueous phase), one phase dispersed in the other. An emulsifying agent is typically included to improve physical stability. Choice of emulsifying agent depends on whether an oil-in-water or a water-in-oil emulsion is desired. In general, to obtain an oil-in-water emulsion, emulsifying agent is chosen having a HLB number (hydrophiliclipophilic balance) below about 10, whereas to obtain a water-in-oil emulsion, emulsifying agent is chosen with a HLB number of 8 and more. There is a certain overlap as indicated in the table below.

| HLB range | Use |
|---|---|
| 0-3 | Antifoaming agents |
| 4-6 | w/o emulsifying agents |
| 7-9 | Wetting agents |
| 8-18 | o/w emulsifying agents |
| 13-15 | Detergents |
| 10-18 | Solubilizing agents |

The emulsifying agents may be anionic, cationic or non-ionic. Examples of anionic emulsifying agents are eg sulfated alcohols such as sulphuric acid esters of fatty alcohols like lauryl or cetyl alcohol. Cationic emulsifying agents are eg quaternary ammonium compounds like cetyltrimethylammonium bromide. Examples of non-ionic emulsifying agents are eg glyceryl esters like glyceryl esters like glyceryl monostearate, polyoxyethylene glycol esters or ethers, sorbitan fatty acid esters like sorbitan monopalmitate, polyoxyethylene derivatives of sorbitan fatty acid esters. etc.

The emulsifying agents mentioned above may also be used in compositions that are not in the form of an emulsion as these agents have surface active properties that may be useful eg as stabilizing agent or as dissolution-improving agents.

A composition of the invention may also be in the form of a suspension. Examples of suspensions are eg dispersions, ointments, liniments, sprays and aerosols. A suspension is a two-phase system, one phase being finely divided solids dispersed in the other phase, which can be a solid, liquid or gas. Normally within the pharmaceutic or cosmetic field a suspension is a dispersion of a solid in a liquid or gas.

Suspensions contains a dispersion medium, which typically is a solvent or mixture of solvents like water, alcohol (ethanol, propanol, isopropanol etc.), propylene glycol, a natural or synthetic oil, a gas etc. It may contain surface active agents (as mentioned above as emulsifying agents), wetting agents (eg alcohol, glycerol), flocculating agents (eg electrolytes), viscosity-increasing agents (eg methylcellulose, carboxymethylcellulose, sodium carboxymethylcellulose, hydroxypropylcellulose, hydroxypropylmethylcellulose, pectin, alginate etc.) as well as additives mentioned below.

Aerosols typically contain pressurised gas such as a fluorocarbon. An aerosol is a product, where the delivery of the active agents is dependent on a liquefied or compressed gas. The active agent is delivered in a finely dispersed mist, foam or semisolid. The aerosol may also contain eg film-forming agents if the resulting composition on the skin is a film containing the active substance. Typical film-forming agents are cellulose and cellulose derivatives including methylcellulose, carboxymethylcellulose, sodium carboxymethylcellulose, hydroxypropylcellulose, hydroxypropylmethylcellulose.

A composition of the invention may be in the form of a gel or hydrogel. A gel typically contains a swellable polymer like cellulose or cellulose derivatives (as those mentioned herein before), pectin, alginate, tragacant, carbomer, polyvinyl alcohols, gelatin, acrylate-based polymers etc.

The composition may also be in the form of an ointment, which is an oleaginous semisolid that contains little if any water. Normally, an ointment is hydrocarbon based such as wax, petrolatum or gelled mineral oil.

A composition of the invention may also contain one or more additive such as pHadjusting agents, buffering agents, viscosity-adjusting agents, aromas, anti-oxidants, moisturizers, preservatives, stabilizers etc.

In the following is given a review of the two drug substances that are object of the present invention.
Triiodothyroacetic Acid (TRIAC)

Triiiodothyroacetic acid (TRIAC) is a thyroidea hormone metabolite (1). In the human body, TRIAC is formed by an oxidative deamination of thyroxine ($T_4$) to tetraiodothyroacetic acid (Tetrac) followed by 5'-deiodination to finally form TRIAC (1). Triiodothyroidine ($T_3$) can also be converted to TRIAC by oxidative deamination (2). Doses greater than 15 times that of $T_3$ (3) and 10 times that of $T_4$ (4) are necessary to obtain similar metabolic effects. It has been shown that TRIAC does not evoke tachycardia as effectively as $T_4$ or $T_3$ (4-5). Thus the therapeutic window for TRIAC is larger than for $T_4$ and $T_3$.

TRIAC has been under clinical investigation since 1957 (3). The administration forms have mainly been oral or injection (4, 6). TRIAC is available on the France market in oral and dermal preparations (7). The 0.2% cream is indicated for the treatment of cellulites. The indication for the oral formulation is Thyroid Stimulation Hormone (TSH) suppression and the recommended doses are 0.7 to 1.75 mg daily. Clinical studies up to 3 weeks with oral administration have shown that daily doses of 3.4 mg are well tolerated (4).

The general toxicity of TRIAC has been studied in two single dose experiments in rats. In a study with intraperitoneal administration of TRIAC suspended in 0.8% hydroxyl propyl methylcellulose gel no observed effect level (NOEL) was found to be 46.4 mg/kg and the lowest lethal dose 100 mg/kg. It was possible to calculate $LD_{50}$ values in this study and they were found to be 143 and 295 mg/kg for male and female rats, respectively. In a study with dermal application on the back of the rats for 24 hours of 2000 mg/kg of TRIAC, suspended as in the intraperitoneal study, neither any clinical signs of general toxicity nor any local irritation at the site of application was observed (3-6).

The local tolerance study of TRIAC cream has been performed in Himalayan rabbits with repeated topical administration, twice a day for 4 weeks. TRIAC cream with three strengths: 0.03%, 0.1% and 0.3%, and with a volume of 0.5 ml was applied on intact skin (left side) and on abraded skin (right side) on the back of the rabbits. In total 24 rabbits were used (3 males and 3 females in each dose group). The control group received the vehicle cream. No substance-related pathological changes were seen—neither macroscopically nor microscopically.

The genotoxic potential of TRIAC has been investigated in the Ames' test and in in vitro chromosome aberration assay in cultured human peripheral lymphocytes. From the results of these tests it can be concluded that TRIAC has no genotoxic potential.

Vitamin A and D derivatives have been used to treat sun damaged skin and skin atrophy (11-13). However, they both have side effects such as skin irritation with redness and scaling. The increase in skin thickness obtained with vitamin A and D derivatives may in fact be due to oedema in both epidermis and dermis and not a protein anabolic effect. With TRIAC no side effects were seen (8-10).

Results from preclinical studies in mice show that topical administration of TRIAC prevents skin atrophy induced by the use of potent topical glucocorticoids (8-10). It can also increase skin thickness of normal skin in mice (9).

Three clinical studies using topical applied TRIAC have been performed by some of the inventors (14-16). The objective of the first study was to investigate the effects of TRIAC 0.1% ointment on psoriasis in a pilot study (14). The conclusion of the study was that topical treatment with TRIAC is safe but no statistically significant effects on psoriasis were found in comparison with placebo. The second study aimed at investigating the effects of TRIAC 0.03% and 0.1% cream on restoring the normal skin collagen synthesis after pre-treatment with topical betamethasone 17-valerate (15). There was a statistically significant increase in both procollagen I and III in both groups compared to placebo 7 days after start of treatment. In the third study patients with skin atrophy on the dorsum of their hands due to topical treatment with potent corticosteroids were treated with a TRIAC 0.1% cream (16). After 8 weeks of treatment skin thickness in both epidermis and dermis was significantly higher in the TRIAC group.

Since the active substance is a thyroid hormone metabolite it can cause symptoms of hyperthyroidism e. g. tachycardia, nervousness, sweating and diarrhoea. The percutaneous penetration from the investigational cream formulation is expected to be low or negligible. In all 3 clinical studies no significant effects were noted on thyroid hormone levels after 8 weeks treatment (14-16). Even other blood analysis showed normal levels (15-16).

Other thyroid hormone analogues as well as naturally occurring thyroid hormones may also have the same beneficial effect in combination with DHEA.

Dehydroepiandrosterone (DEAH)

Dehyroepiandrosterone (DHEA) is a steroid hormone produced and secreted from the adrenal cortex. It is found in high concentration in the blood stream from mid childhood, peaks in early adulthood and declines then with increasing age. DHEA is considered a weak androgen as it is metabolized into testosterone and estradiol in peripheral tissues. It is thought that its action is through the testosterone and oestrogen receptors, but there is still an ongoing debate on whether DHEA may have own effects through its own or other receptors. When administered by oral route it has a positive effect on skin conditions in elderly people (19). In an open study a DHEA 1% formulation or the vehicle was topically applied to fascial and hand skin for 4 months, in two groups of 20 post-menopausal women. The result of this pilot study was that topical DHEA, but not the vehicle, improved skin brightness and counteract papery appearance of the skin and epidermal atrophy which are characteristic features of skin aging.

Alternatively or additionally to DEAH anabolic steroids may be used such as androstenedione, dihydrotestosterone, apotone, oxandrolone, oxabolone, nandrolone or testosterone. Specifically a combination of TRIAC, DEAH and testosterone is of interest.

Other studies have been performed in postmenopausal women (20, 21) and the results given in (21) indicate that DHEA may have an anti-aging effect on the skin.

The invention is illustrated in the following non-limiting examples

Example 1

Synergistic Effect of a Combination of TRIAC and DHEA

The aim of the present study was to demonstrate if an additive or synergistic effect of topical TRIAC and DHEA on procollagen I synthesis in skin was found.

Material and Methods

Subjects.

Six healthy male volunteers aged 40-65 years. Criteria for exclusion are: treatment with systemic or topical glucocorticoids, ongoing serious infections, immunosuppression.

Study Formulations.

TRIAC and DHEA were obtained from Sigma. They were mixed with Essex cream (Merck) to obtain 4 different study formulations:

A. 0.03% TRIAC in Essex cream
B. 0.03% TRIAC and 2% DHEA in Essex cream
C. Essex cream alone.
D. 2% DHEA in Essex cream Essex cream is a cream that contains white soft paraffin wax (150 mg/g) and paraffin oil (also denoted liquid paraffin) (60 mg/g). Other ingredients are concentrated phosphoric acid, purified water, cetostearyl alcohol, macrogolcetostearyl ether, sodium dihydrogenphosphate dihydrate and chlorcresol. It is marketed in the Nordic countries by Merck, Sharp & Dome.

Study Design.

A proof-of-concept, single blinded, open prospective study comparing, TRIAC, DHEA and the combination of the two as compared with non-active treatment on short-term glucocorticoid-induced skin atrophy.

The test area was normal looking abdominal skin in 6 male volunteers. Four different skin areas of 10×10 cm were marked with a permanent marker pen.

All areas were pretreated twice daily with betametasone valerate (Betnovate, GSK) 0.5 gr twice daily for 21 days. Then each test area was treated, with 0.5 gr twice daily of one of the test formulations, for 14 days.

Suction-Induced Skin Blisters.

Suction blisters were induced with a disposable device (Dermovac, Ventipress, Lappeeranta, Finland) placed on the test areas and connected to a vacuum pump with a vacuum of approximately 60 mm Hg. Each device produces five suction blisters within approximately one hour. The resulting fluid was collected, using a syringe, and then combined and frozen at −70° C.

Analysis of Amino Terminal Propeptide of Human Type I Procollagen (PINP) in Suction Blister Fluid.

Analysis for PINP was performed from suction blister fluid obtained after 14 days treatment with the test formulations using a commercially available RIA kit. (UniQ PINP RIA, Orion Diagnostics, Espoo, Finland; Detection limit 2 μg/L; intra-assay coefficient of variation, 5.4%; inter-assay coefficient of variation, 9.5%).

Statistics.

Paired comparison was made between the four different treatments using the Kruskal-Wallis test.

Results

Suction blisters were produced successfully in all volunteers and suction blister fluid was stored for analysis of human type I procollagen (PINP) from all volunteers.

In Table 1 the mean value for all four different alternatives (TRIAC, TRIAC+DHEA, DHEA and placebo) is presented. The statistical analysis demonstrated a significant treatment effect. The PINP concentration was lowest in the placebo treated area. PINP increased by treatment from DHEA, TRIAC and the combination of TRIAC and DHEA demonstrating the highest concentration. The results show that treatment with DHEA is only slightly better than treatment with placebo. However, the combination of TRIAC and DHEA improves the effect markedly and demonstrate a synergistic effect between the two drug substances.

Table 1. The mean values for analysis of Procollagen I (PINP) (μg/l) in four skin areas pre-treated with betamethasone valerate for 3 weeks. The skin areas were then treated with one of the following alternatives: A: TRIAC, B: TRIAC+DHEA, C: Placebo, D: DHEA for 2 weeks.

| | |
|---|---|
| A. TRIAC | 555 |
| B. TRIAC + DHEA | 729 |
| C. Placebo | 257 |
| D. DHEA | 279 |

Discussion

In earlier studies in mice it has been shown that TRIAC alone in concentrations of 0.03% could restore skin thickness in mice pretreated with betamethasone valerate (8-9). In human healthy volunteer's treatment with a TRIAC 0.03% cream was significantly more effective in stimulating PINP synthesis, in skin pretreated with betamethasone valerate, compared to placebo (15). In another study topical treatment with TRIAC appears to reverse glucocorticoid-induced skin atrophy in patients treated with potent topical corticosteroids for hand eczema (16).

DHEA is a steroid hormone involved in physiological aging. When administered by oral route it has a positive effect on skin conditions in elderly people (19).

In another study involving post-menopausal women the results indicate the possibility that topically applied DHEA could exert an anti-aging effect in the skin through stimulation of collagen biosynthesis, improved structural organization of the dermis and modulating keratinocyte metabolism (20).

In our study we have for the first time shown that a combination of TRIAC and DHEA could effectively stimulate PINP synthesis in skin pretreated with betamethasone valerate and that the combination was more effective than TRIAC or DHEA alone. This combination could be used to effectively treat skin atrophy in corticosteroid induced skin atrophy. It could also be used to treat skin atrophy due to other circumstances such as e. g. sun damaged skin and skin atrophy due to high age. Another interesting application would be to combine TRIAC and DHEA with a potent corticosteroid in order to prevent corticosteroid-induced skin atrophy. If this combination still is effective in the treatment of eczema and psoriasis and without the risk of skin atrophy this combination will be a major breakthrough for the use of potent topical corticosteroids.

In the following examples are given of compositions of the invention. They are not intended to limit the invention in any way.

Formulation Examples

In the following are given formulation examples, i.e. examples on vehicles suitable for use in the present invention. TRIAC and DHEA, and optionally a corticosteroid, are typically added to the vehicles or they may be dissolved in one or more of the ingredients optionally by use of heating to max. 80° C. Details relating to preparatory methods and to further examples of suitable vehicles are found in Remington's Pharmaceutical Sciences, eg 18$^{th}$ ed. Mack Publishing Company, 1990.

Formulation Example 1

| A lotion base to use in preparing a composition of the invention | |
|---|---|
| Zinc Oxide | 8 g |
| Glycerine | 2 ml |
| Avicel ® Gel | 2 g |
| Carboxymethylcellulose | 2 g |
| Calcium hydroxide solution | ad 100 ml |

Formulation Example 2

| o/w emulsion | |
|---|---|
| Liquid petrolatum (HLB 10.5) | 50 g |
| Emulsifying agent | 5 g |
| Sorbitan monooleate (HLB 4.3) | |
| Polyoxyethylene 20 sorbitan monooleate (HLB 15) | |
| Water | ad 100 ml |

Formulation Example 3

| Ointment | |
|---|---|
| 1 g ointment contains: | |
| Paraffin liquid | 30 mg |
| Alpha-tocopherol | 20 μg |
| White soft paraffin | to make 1 g |

Formulation Example 4

| A sprayable composition | |
|---|---|
| 1 g contains | |
| Hydroxymethylcellulose | 150 mg |
| Ethanol | to make 1 g |

Formulation Example 5

| A lotion | |
|---|---|
| 1 g contains | |
| Disodium phosphate dehydrate | 2.5 mg |
| Diazolidinyl urea | 3 mg |
| Polyoxypropylene-15 stearyl ether | 50 mg |
| Brij ® 72 | 30 mg |
| Water, purified | to make 1 g |

REFERENCES

1. Braverman L E, Utiger R D (ed). In Werner and Ingbar's. The Thyroid (ed 7) Philadelphia. Lippincott-Raven Publishers, Chapter 8, 1996:127.

2. Braverman L E, Utiger R D (ed). In Werner and Ingbar's. The Thyroid (ed 7) Philadelphia. Lippincott-Raven Publishers, Chapter 7, 1996:562.
3. Rall J E, Pearson O H, Lipsett M B, Rawson R W. Metabolic effects in man of the acetic acid analogues of thyroxine and triiodothyropnine. J Clin Endocrinol Metab 1956; 16:1299-1310.
4. Bracco D, Morin O, Schutz Y, Liang H, Jequier E, Burger A G. Comparison of the metabolic and endocrine effects 3,5,3'-Triiodothyroacetic acid and thyroxine. J Clin Endocrinol Metab 1993; 77:221-228.
5. Bentin J, Desir D, Mockel J. TriAC (3,5,3'-Triiodothyroacetic acid) induced pseudohypothyroidism. Acta Clin Belg 1984; 39:285-289.
6. Burger A G, Engler D, Sakoloff C, Stacheli V. The effects of tetraiodothryoacteic and triiodothyroacetic acids on thyroid function in euthyroid and hyperthyroid subjects. Acta Endocrinologica 1979; 92:455-467.
7. Directonaire Vidal (1995). Product information on Tricana ills and on Triacana cream.
8. Faergemann J, Sarnhult T, Hedner E, Zhao X-H, Sun X-Y, et al. Dose-response effects of tri-iodothyroacetic acid (TriAc) and other thyroid bhormone analogs on glucocorticoid induced skin atrophy in the mouse. Acta Derm Venereol 2002; 82:179-183.
9. Yazdanparast P, Carlsson B, Sun X-Y, Chao X-H, Hedner T, Faergemann J. Action on topical thyroid hormone analogues on glucocorticoid-induced skin strophy in mice. Thyroid 2006; 16:273-280.
10. Safer J D, Fraser L M, Ray S, Holick M F. Topical triiodothyronine stimulates epidermal propiferation, dermal thickening and hair growth in mice and rats. Thyroid 2001; 11:717-724.
11. Gniadecki R, Gniadecki M, Serup J. Inhibition of glucocorticoid-induced epidermal and dermal atrophy with KH-1060—a potent 20 epi-analogue of 1,25-dihydroxyvitamin $D_3$. Br J Dermatol 1994; 113:439-444.
12. Gniadecki R, Gniadecki M, Serup J. The effects of KH-1060, a potent 20 epi analogue of the vitamin $D_3$ hormone, on hairless mouse skin in vivo. Br J Dermatol 1995; 132:841-852.
13. Schwartz E, Mezick J, Gendimenico G, Kligman L. In vivo prevention of corticosteroid-induced skin atrophy by tretinoin in the hairless mouse is accompanied by modulation of collagen, glucosaminoglycans, and fibronection. J Invest Dermatol 1994; 102:241-246.
14. Vahlquist A, Törmä H, Carlsson B. Inefficacy of topical thyroid hormone analogue TriAc in plaque psoriasis: results of a double-blind placebo-controlled trial. Br J Dermatol 2004; 15:489-491.
15. Yazdanparast P, Carlsson B, Oikarinen A, Risteli J, Faergemann J. A thyroid hormone analogue, triiodothyroacetic acid, corrects corticosteroid-down regulated collagen synthesis. Thyroid 2004; 14:345-353.
16. Yazdanparast P, Carlsson B, Oikarinen A, Risteli J, Lavin T, Faergemann J. Action of topical thyroid hormone analogue, triiodothyroacetic acid in reversing glucocorticoid-induced skin atrophy in humans. Thyroid 2006; 16:1157-1162.
17. Patent EP 0831769 (B1 and B2). Novel uses for thyroid hormones or thyroid hormone-like compounds. Inventor Thomas N. Lavin.
18. Report of the patent and patent protection of EP 0831769 and related patent and patent applications. Strom and Gulliksson 2007 and 2008.
19. Nouveau S, Bastien P, Baldo F, de Lacharriere O. Effects of topical DHEA on aging skin: A pilot study. Maturitas 2008; 59:174-181.
20. El-Alfy M, Deloche C, Azzi L, Bernard B A, Bernerd F, Coutet J, Chaussade V, Martel C, Leclaire J, Labrie F. Skin responses to topical dehydroepiandrosterone: implications in antiageing treatment? Br J Dermatol. 2010; 163:968-76.
21. Calvo E, Luu-The V, Morissette J, Martel C, Labrie C, Bernard B, Bernerd F, Deloche C, Chaussade V, Leclaire J, Labrie F. Pangenomic changes induced by DHEA in the skin of postmenopausal women. J Steroid Biochem Mol Biol. 2008 December; 112(4-5):186-93.

The invention claimed is:
1. A topical composition comprising triiodothyroacetic acid (TRIAC) and dehydroepiandrosterone (DHEA).
2. The composition according to claim 1, further comprising a topically acceptable vehicle.
3. The composition according to claim 1, containing from 0.01 to 2% w/w TRIAC.
4. The composition according to claim 1, containing from 0.01 to 0.5% w/w TRIAC.
5. The composition according to claim 1, containing from 0.5 to 5% w/w DHEA.
6. The composition according to claim 1, containing from 1 to 3% w/w DHEA.
7. The composition according to claim 1, wherein the w/w ratio of DHEA to TRIAC is from about 10 to about 200.
8. The composition according to claim 1, wherein the w/w ratio of DHEA to TRIAC is from about 60 to about 70.
9. The composition according to claim 1, further comprising a corticosteroid.
10. The composition according to claim 1, in the form of an ointment, cream, lotion, liniment, solution, dispersion, emulsion, suspension, gel, liposome formulation, sprayable composition, aerosol, film, powder, wash, or shampoo.

* * * * *